United States Patent [19]

Atkinson

[11] Patent Number: 5,703,046
[45] Date of Patent: *Dec. 30, 1997

[54] TREATMENT METHOD USING RECOMBINANTLY PRODUCED HUMAN MEMBRANE COFACTOR PROTEIN (MCP)

[75] Inventor: John P. Atkinson, St. Louis, Mo.

[73] Assignee: Washington University, St. Louis, Mo.

[*] Notice: The term of this patent shall not extend beyond the expiration date of Pat. No. 5,552,381.

[21] Appl. No.: 476,713

[22] Filed: Jun. 7, 1995

Related U.S. Application Data

[62] Division of Ser. No. 948,350, Sep. 21, 1992, Pat. No. 5,514,787, which is a continuation of Ser. No. 384,210, Jul. 21, 1989, abandoned.

[51] Int. Cl.$^6$ .......... A61K 38/17; C07K 14/47; C07K 14/705; C12P 21/00
[52] U.S. Cl. .......... 514/12; 530/380; 530/350; 435/69.1; 435/348; 435/349; 435/252.3; 435/254.11
[58] Field of Search .......... 514/12; 530/380; 435/183, 69.1, 240.1, 252.3, 254.11, 320; 536/23.5

[56] References Cited

U.S. PATENT DOCUMENTS 5,552,381  9/1996  Atkinson .......... 514/8

FOREIGN PATENT DOCUMENTS 8901041  2/1989  WIPO.

OTHER PUBLICATIONS

Seya, et al. (1986) J. Exp. Med., 163: 837–855.
Johnson (1977) J. Pharm Sci. 66(10) 1367–1377.
Norbiato, et al. (1986) J. Clin. Endocrinol. Metab., 63 (3): 747–750 (Abstract furnished).
Reid, et al., Immunol. Today (1986) 7:230–234.
Yu, et al., J. Clin. Invest. (1986) 78:494–501.
Medof, et al., Proc. Natl. Acad. Sci. (1987) 84:2007–2011.
Caras, et al., Science (1987) 238:1280–1283.
Ballard, et al., J. Immunol. (1987) 138:3850–3855.
Seya, et al., Eur. J. Immunol. (1988) 18:1289–1294.
Seya, et al., Complement (1987) 4:225.
Hourcade, et al., Adv. Immunol. (1989) 45:381–416.
Lublin, et al., Ann. Rev. Immunol. (1989) 7:35–58.
Lublin, et al., J. Exp. Med. (1987) 165: 1731–1736.
Cole, et al., Proc. Natl. Acad. Sci., (1985) 82:859–863.
Lublin, et al., J. Exp. Med. (1988) 168:181–194.
Ballard, et al., J. Immunol. (1988) 141(11):3923–3929.
McNearney, et al., J. Clin. Invest. (1989) 84:001–008.
Stafford et al., Proc. Natl. Acad. Sci. (1988) 85:880–884.
Bora et al., J. Exp. Med. (1989) 169:597–602.
Farries et al., Complement and Inflamm. (1990) 7:30–41.
Lublin et al., Current Topics in Micro. and Immunology (1989) 153: 123–145.
Hourcade et al., Progress in Immunology (1989) vol. VII:171–177.
Seya et al., (1989) Biochem. J. 164, 7 pages of text.
Holers, et al., Immunol. Today (1985) 6:188–192.
Ross, et al., Adv. Immunol. (1985) 37:217–267.
Atkinson, et al., Immunol. Today. (1987) 8:212–215.
Purcell et al., Immunology (1990) 70: 155–161.
Kim, J. Biol. Chem. (1989) 264(17):9780–9784.
Wong et al., J. Immunol. (1985) 134(6):4048–4056.
Goujet–Zalc et al., Cell. Immunol. (1987) 109:282–294.
Cui et al., FASAB J. (1989) 3:A500, No. 1594.
Seya et al., Biochem. J. (1989) 264:(7 pages of text total).

Primary Examiner—Stephen Walsh
Assistant Examiner—Claire M. Kaufman
Attorney, Agent, or Firm—Arnall Golden & Gregory, LLP

[57] ABSTRACT

Human membrane cofactor protein, a protein involved in regulation of complement activity, has been purified to homogeneity. The gene encoding this protein has been retrieved and permits deduction of the entire amino acid sequence and the recombinant production of this material. Pharmaceutical compositions in which MCP is the active ingredient for use in treating antoimmune diseases are also disclosed.

6 Claims, 3 Drawing Sheets

```
TCTGCTTCCTCCGGAGAAATAACAGCGTCTCTTCCGCGCCGCGGAGCCTCCCGGCCGCGGAGTGTCCC    73
                                    M  E  P  P  P  G  R  R  E  C  P     25
                                   -34

TTTCCTTCCTGGCTTCCTGGTTGCTCTGCGGCCATGGCGGTGCTGCTGTACTCCTTCTCCGATGCC     145
 F  P  S  W  R  F  P  G  L  L  L  A  A  M  V  L  L  L  Y  S  F  S  D  A    1
                                                                    -1

TGTGAGGAGCCACCAACATTTGAAGCTATGGAGCTCATTGGTAAACCAAAACCCTACTATGAGATTGGTGAA  217
 C  E  E  P  P  T  F  E  A  M  E  L  I  G  K  P  K  P  Y  Y  E  I  G  E   24
+1

CGAGTAGATTATAAGTGTAAAAAGGATACTTCTATATACCTCCTTGCCACCCATACTATTGTGATCGG      289
 R  V  D  Y  K  C  K  K  G  Y  F  Y  I  P  P  L  A  T  H  T  I  C  D  R   48

AATCATACATGGCTACCTGTCTCAGATGACGCCTGTTATAGAGAAACATGTCCATATATACGGGATCCTTTA  361
 N  H  T  W  L  P  V  S  D  D  A  C  Y  R  E  T  C  P  Y  I  R  D  P  L   72

AATGGCCAAGCAGTCCCTGCAAATGGGACTTACGAGTTGGTTATCAGATGCACTTATTGTAATGAGGGT    433
 N  G  Q  A  V  P  A  N  G  T  Y  E  F  G  Y  Q  M  H  F  I  C  N  E  G   96

TATTACTTAATTGGTGAAGAAATTCTATATTGTGAACTTAAAGGATCAGTAGCAATTTGGAGCGGTAAGCCC  505
 Y  Y  L  I  G  E  E  I  L  Y  C  E  L  K  G  S  V  A  I  W  S  G  K  P   120

CCAATATGTGAAAAGTTTGTGTACACCACCTCCAAAAATAAAAATGAAAACACACCTTTAGTGAAGTA     577
 P  I  C  E  K  V  L  C  T  P  P  P  K  I  K  N  G  K  H  T  F  S  E  V   144
```

FIG. 1-1

```
GAAGTATTTGAGTATCTTGATGCAGTAACTTATAGTTGTGATCCTGCACCTGGACCAGATCCATTTTCACTT   649
 E  V  F  E  Y  L  D  A  V  T  Y  S  C  D  P  A  P  G  P  D  P  F  S  L    168

ATTGGAGAGAGCACGATTATTGTGGTGACAATTCAGTGTGGAGTCGTGCTCCAGAGTGTAAAGTGGTC       721
 I  G  E  S  T  I  Y  C  G  D  N  S  V  W  S  R  A  A  P  E  C  K  V  V    192

AAATGTCGATTCCAGTAGTCGAAAATGGAAAAACAGATATCAGGATTTGGAAAAATTTACTACAAAGCA      793
 K  C  R  F  P  V  V  E  N  G  K  Q  I  S  G  F  G  K  K  F  Y  Y  K  A    216

ACAGTTATGTTTGAATGCGATAAGGGTTTTTACCTCGATGGCAGCGACACAATTGTCTGTGACAGTAACAGT   865
 T  V  M  F  E  C  D  K  G  F  Y  L  D  G  S  D  T  I  V  C  D  S  N  S    240

ACTTGGGATCCCCCAGTTCCAGTTCCAAATCTTCCACTACAAATCTTCCAGCGTCCAGT                937
 T  W  D  P  P  V  P  P  V  P  K  C  L  K  V  S  T  S  S  T  T  K  S  P  A  S  264

GCCTCAGGTCCTAGGCCTACTTACAAGCCTCCAGTCTCAAATTATCCAGGATATCCTAAACCTGAGGAAGGA  1009
 A  S  G  P  R  P  T  Y  K  P  P  V  S  N  Y  P  P  G  Y  P  K  P  E  E  G  288

ATACTTGACAGTTTGGATGTTTGGGTCATTGCTGTGATTGTTATTGCCATAGTTGTTGGAGTTGCAGTAATT  1081
 I  L  D  S  L  D  V  W  V  I  A  V  I  V  I  A  I  V  V  G  V  A  V  I    312

TGTGTTGTCCCGTACAGATCTTCAAAGGAGGAAGAAGAAAGGAAGCAGATGGTGGAGCTGAATATGCC      1153
 C  V  V  P  Y  R  Y  L  Q  R  R  K  K  K  G  K  A  D  G  G  A  E  Y  A    336
```

FIG. 1-2

```
ACTTACCAGACTAAATCAACCACTCCAGCAGAGAGGCTGAATAGATTCCACAACCTGGTTTGCCAGT  1225
 T  Y  Q  T  K  S  T  T  P  A  E  Q  R  G  *                         350

TCATCTTTTGACTCTCTATTAAATCTTCAATAGTTGTTATTCTGTAGTTTCACTCTCATGAGTGCAACTGTGG  1297

CTTAGCTAATATTGCAATGTGGCTTGAATGTAGGTAGCATCCTTTGATGCTTCTTGAAACTTGTATGAATT  1369

TGGGTATGAACAGATTGCCTGCTTTCCCTTAAATAACACTTAGATTTATTGGACCAGTCAGCACAGAGCATGCC  1441

TGGTTGTATTAAAGCAGGGATATGCTGTATTTTATAAAATTGGCAAAATTAGAGA<u>AATATA</u>GTTCA<u>AATGA</u>  1513

<u>A</u>ATTATATTTTCTTTGTAAAAAAAAAAAAAA  1546
```

FIG.1-3

TREATMENT METHOD USING RECOMBINANTLY PRODUCED HUMAN MEMBRANE COFACTOR PROTEIN (MCP)

This is a divisional of U.S. Ser. No. 07/948,350 entitled "Recombinantly Produced Human Membrane Cofactor Protein (MCP)", filed Sep. 21, 1992, by John P. Atkinson now U.S. Pat. No. 5,514,787, which is a continuation of U.S. Ser. No. 07/384,210 filed Jul. 21, 1992 now abandoned.

TECHNICAL FIELD

The invention is related to human therapeutics and regulation of the complement cascade. More specifically, it concerns the recombinant production of human membrane cofactor protein (MCP) which is an important factor in the regulation of complement cascade.

BACKGROUND ART

The complement system is capable of tissue and cell destruction and is therefore a major element of the defense system against invasion by foreign tissue. However, control of this system is necessary in order to prevent destruction of autologous cells. A large number of proteins which are involved in control of the complement cascade have been described.

Most relevant to the present invention is the group which controls the C3 convertase stage of the cascade and binds to fragments of either C3 or C4 or both. This group includes serum proteins such as C4-binding protein and factor H and membrane proteins such as C3b receptor, C3d/Epstein-Barr virus receptor, decay-accelerating factor (DAF), and the protein of the invention, membrane factor protein (MCP). Reviews of these various factors and their role in complement cascade regulation can be found in Holers, B. M., et al., *Immunol Today* (1985) 6:188; Ross, G. D., et al., *Adv Immunol* (1985) 37:217; Atkinson, J. P., et al., *Immunol Today* (1987) 8:212.

Much is known concerning these regulatory proteins, except for MCP. They are each composed of multiple repeat of an approximately 60-amino acid consensus sequence composed of conserved cys, pro, gly, trp, leu/ile/val, and tyr/phe residues (Reed, K., et al., *Immunol Today* (1986) 7:230. The genes encoding these proteins have been localized to the long arm of human chromosome 1, band 1q32 and form a multigene family designated the regulator of complement activation (RCA) gene cluster. As will be shown below, MCP is also a member of this family.

A member of this family particularly related to the MCP of the invention is the decay-accelerating factor (DAF) which was identified on human platelets by Yu, G. H., et al., *J Clin Invest* (1986) 78:494–501. DAF is present on virtually all peripheral blood cells, including erythrocytes, granulocytes, T and B lymphocytes, monocytes, and platelets; in addition, soluble forms of DAF have been found in extracellular fluids and tissue culture supernatants. The gene encoding DAF has been cloned and sequenced (by Medof, M. E., et al., *Proc Natl Acad Sci USA* (1987) 84:2007–2011; and by Caras, I. W., et al., *Science* (1987) 238:1280–1283). It has been shown that the membrane and soluble secreted forms of DAF result from differential splicing of the mRNA encoding these proteins with the soluble form having a longer C-terminus, but a C-terminus which lacks the membrane binding region associated with the membrane DAF, as described in PCT application WO89/01041.

MCP was initially identified by iC3/C3b affinity chromatography on surface-labeled peripheral blood cells and designated gp45–70 to describe the range of $M_r$ obtained on SDS-PAGE (Cole, J. L., et al., *Proc Natl Acad Sci USA* (1985) 82:859. MCP was partially purified from the human mononuclear cell lines and shown to have a cofactor activity but no decay accelerating function (Seya, T. J., et al., *J Exp Med* (1986) 163:837. MCP is absent from erythrocytes, but present as a membrane-bound protein on human T and B lymphocytes, granulocytes, monocytes, platelets, endothelial cells, epithelial cells, and fibroblasts; on most of these cells it occurs in polymorphic forms of molecular weight 63 kd and 58 kd, as determined by SDS-PAGE. These appear to result from a two allelic system encoding MCP (Ballard, L., et al., *J Immunol* (1987) 138:3850–3855). The MCP found by immunoprecipitation on the membranes of granulocytes appears, however, not to exhibit this polymorphism (Seya, T., et al., *Eur J Immunol* (1988) 18:1289–1294). The occurrence of MCP on a wide range of host cells is consistent with a role in protecting host cells from damage by complement (Seya, T. L., et al., *Complement* (1987) 4:225.

The previously purified MCP has been utilized to prepare a polyclonal rabbit antiserum monospecific for this protein. The antisera were raised in rats by repetitive injections of MCP purified as described by Seya, T., et al., *J Exp Med* (1986) (supra), in complete Freund's adjuvant. These antisera have been used to identify MCP in extracts from various membranes.

The present invention provides a more highly purified form of this protein and the capacity to produce it recombinantly, thus providing practical quantities for therapeutic use.

DISCLOSURE OF THE INVENTION

Human membrane cofactor protein (MCP) is a significant protector of host tissue from autologous destruction by the complement system. Practical quantities of this protein and antibodies specifically immunoreactive with it are made available by recombinant production of human MCP.

Accordingly, in one aspect, the invention is directed to purified and isolated human MCP and to human MCP produced recombinantly. In other aspects, the invention is directed to recombinant materials and methods which result in the manufacture of useful quantities of this protein. Also an aspect of the invention are antibodies immunoreactive with the protein which are useful in diagnosis of disorders associated with reduced or elevated amounts of MCP. Further, the invention includes genetic probes useful in detecting polymorphisms of the MCP-encoding gene, and in obtaining DNA encoding corresponding MCP in other species.

In still further aspects, the invention is directed to pharmaceutical compositions containing the MCP of the invention and to methods of treating or ameliorating inflammatory and autoimmune conditions mediated by an excess or misdirection of complement activity.

In still another aspect, the invention is directed to methods to diagnose abnormalities in the immune system, specifically the presence or absence of autoimmune disease by assessing the levels of MCP present on peripheral blood cells and to a method to predict the probability of recurrent miscarriage by testing elevated levels of MCP in the placenta.

BRIEF DESCRIPTION OF THE DRAWINGS

FIG. 1 shows the nucleotide sequence and deduced amino acid sequence of human MCP.

MODES OF CARRYING OUT THE INVENTION

As used herein, human MCP refers to a protein which shows complement-inhibitory activity according to standard hemolysis assays described below, has cofactor activity according to the assay of Turner, J. R., et al., Masters Thesis, Washington U., St. Louis, Mo. (1984), incorporated herein by reference; is free of decay-accelerating function as assayed according to Hoffmann, E. M., *Immunochemistry* (1969) 6:405–419, incorporated herein by reference, and has an amino acid sequence referenced to that shown as amino acids 1–350 in FIG. 1 herein. By "referenced to" is meant that the protein contains the same amino acid sequence as that shown, is encoded by a DNA which represents an allelic variant of the DNA encoding the amino acid sequence shown, or has an amino acid sequence which has deletions, insertions, and/or substitutions of individual or multiple amino acid residues which do not alter the qualitative pattern of activity described. For example, and specifically included among amino acid sequences referenced to that shown in FIG. 1, are those in which the membrane binding region indicated by the boldface underline in the figure is deleted, along with allelic variants of the remaining portion. The protein in soluble form is thus specifically included.

With respect to deletions and insertions, preferred are those wherein only one, two or a small number of amino acid residues in the first 238 amino acid sequence of the mature protein, before the arrow at residue 239, are inserted or deleted, More substantial alterations can be made downstream of this arrow. Preferred substitutions are those which are conservative—i.e., hydrophobic amino acids substituted for hydrophobic amino acids, positively charged amino acids for positively charged, etc. Thus, preferred substitutions are glu for asp and vice versa, lys for his for arg and permutations thereof; substitutions among the group ile, val, met, and leu; substitutions among the group gly, ala, ser and cys; and substitutions among the group trp, tyr, and phe.

As is understood in the art, the protein may exist in a variety of ionization states depending on the pH conditions in which it is prepared. Thus, the MCP protein may exist in the salt form (salts formed from bases as to the carboxyl groups or acid addition salts as to the amino groups). Furthermore, the protein may be derivatized in various ways, including glycosylation, acylation, sulfation, and the like. It is believed that as glycosylation is a post-translational process, the glycosylation pattern is dependent on the nature of the cell in which the protein is produced. Differences in glycosylation pattern are particularly understood to be relevant to the present case. For example, it has been shown that the dimorphic character of the MCP extracted from membranes of various peripheral blood cells is in part accounted for by the difference in quantity of sialic acid in the two forms (Ballard, L. L., et al., *J Immunol* (1988) 141:3923–3929, incorporated herein by reference). According to this disclosure, the two forms of MCP derived from human mononuclear cells and cell lines are shown to have three of four peptides obtained by peptide mapping which are identical, whereas the largest partially digested peptide is different, and the difference in sialic residues accounts for most of the molecular weight difference between the two species.

As shown in FIG. 1, the DNA encoding the human MCP from the human T cell line HSB2 is now available in the art. DNA encoding this particular embodiment can be obtained as described in the Examples below or, preferably, can be synthesized de novo using known techniques. Alternatively, partial cloned sequences can be ligated to synthetic portions. Alterations in the sequence shown in FIG. 1 can be incorporated into the de novo synthesis or can be obtained from previously synthesized or cloned DNA using site-directed mutagenesis, as is known in the art per se. Provision of and disclosure of the complete amino acid sequence for the protein acting as a cofactor, as shown in residues 1–238 of FIG. 1, permit synthesis of DNAs encoding not only this sequence, with or without the membrane-attaching portion thereof, but also alternate forms which are referenced to the protein shown as 1–350 in FIG. 1.

The DNA is preferably provided with linkers for ligation into cloning and expression vectors. Techniques for preparation of such vectors are well understood in the art. The DNA encoding the desired MCP is ligated in operable linkage with control sequences, including promoters, upstream enhancers, termination sequences, and so forth, depending on the nature of the intended recombinant host cells. Technology is currently available for expression of heterologous genes, including MCP in its various forms, in a variety of hosts, including procaryotic hosts and various eucaryotes, including yeasts, mammalian or avian or insect cells, and plant cells. The choice of control sequences and markers in the expression vectors is selected appropriately to these hosts.

For example, in procaryotic hosts, various promoters, including inducible promoters such as the trp promoter and lambda phage $P_L$ promoter can be employed. Hybrid promoters such as the tac promoter, which contains the trp polymerase binding region in combination with the lactose operator, can be used. Suitable markers are generally those related to antibiotic resistance. On the other hand, in mammalian cell cultures, commonly used promoters are virally derived, such as the early and late SV40 promoters, adenovirus promoters, metallothionein-II promoter, and the like. Some of these promoters are also capable of being regulated by conditions in the medium, such as the metallothionein-II promoter, which is regulated by glucocorticoids or heavy metals. These promoter systems are compatible with typical mammalian hosts, most commonly Chinese hamster ovary (CHO) cells.

Another commonly employed system is the baculovirus expression system compatible with insect cells. Plant cells, used in conjunction with, for example, the nopaline synthetase promoter, and yeast cells, used in conjunction with promoters associated with enzymes important in the glycolytic pathway, can also be employed. A number of suitable expression systems can be found in appropriate chapters in "Current Protocols in Molecular Biology," Ausubel, F. M., et al., eds., published by Wiley Interscience, latest edition.

Although greatly more laborious, the desired MCP peptide, now that its amino acid sequence has been elucidated by sequencing of the gene, could be synthesized by standard amino acid coupling techniques to obtain smaller peptides which could then be coupled using known techniques.

Regardless of the mode of preparation, whether recombinant or synthetic (or, indeed, by isolation from nature sources), the MCP is purified using techniques analogous to those described by Ballard et al., *J Immunol* (1988) (supra).

The purified protein is then formulated for administration using techniques known generally to treat or alleviate the symptoms of diseases and conditions characterized by excessive complement activity. Such diseases include autoimmune diseases, for example, rheumatoid arthritis, systemic lupus erythematosis, thyroiditis, myasthenia gravis, multiple sclerosis; and other diseases which are characterized by inflammation, such as arteritis of serum sickness, proteinuria in acute nephrotoxic nephritis, kidney inflammation, including glomerulitis, and insulin-dependent diabetes myelitis.

The MCP is generally formulated for injection, either systemically or directly to the tissues affected. Suitable formulations can be found, for example, in *Remington's Pharmaceutical Sciences* (1985), Mack Publishing Company, Easton, Pa., latest edition. For injection, the protein is dissolved or suspended in liquid medium, for example, Hank's solution, Ringer's solution, dextrose solution, and various buffers. Additional excipients such as stabilizers can also be employed.

Besides injection, the peptides of the invention can be administered systemically, via suppository, oral administration, transmucosal administration, including intranasal sprays, and by slow release formulations. Additional formulation techniques include encapsulation formulations, such as liposomes.

Finally, the peptides of the invention can be conjugated to target-directing ligands to carry them to the site of desired bioactivity. Such ligands can include, most commonly, immunoglobulins or their fragments and ligands specific for cell-associated receptors. Targeted forms of the MCP are particularly useful in treating allograft rejections by targeting the foreign tissue.

In addition to utility as a therapeutic, the MCP can be used to raise polyclonal antisera or to produce cells which can be fused to immortalizing partners to obtain sources of monoclonal antibodies specific for MCP. These antibodies are useful as a passive therapeutic to treat diseases which are characterized by low complement activity, or to remedy deficiencies in the complement system, and also to raise antiidiotypic antibodies which are, in turn, therapeutically useful. The antibodies of the invention are also useful diagnostic tools for assay of MCP levels on peripheral blood cells or other normally MCP-bearing cells using standard immunoassay techniques.

The cDNA of the invention, homologous to that shown in FIG. 1, is also useful as a probe to recover analogous MCP-encoding DNAs in a variety of species, in addition to human. This cDNA or its homologs can be used diagnostically as a probe to detect elevated levels of MCP in placental tissue; these elevated levels are predictive of propensity for miscarriages in future pregnancies.

The following examples are intended to illustrate but not limit the invention.

EXAMPLE 1

Preparation of Purified Human MCP

The procedure of Seya, T., et al., *J Exp Med* (1986) 163:837, cited above, and incorporated herein by reference was employed. The protein was purified from the T cell line HSB2 by solubilization in NP-40 followed by sequential chromatography on chromatofocusing, hydroxyapatite, C3 (methylamine) Sepharose, and Mono Q columns. Approximately 20 ug of partially purified protein thus obtained was subjected to 10% SDS-PAGE and the 63 kd $M_r$ band was electroeluted and electrodialyzed according to the procedure of Hunkapiller, M. W., et al., *Meth Enzymol* (1983) 91:227. The resulting protein was homogeneous according to the criteria of SDS-PAGE and HPLC.

EXAMPLE 2

Recovery of cDNA-encoding MCP

The monocyte U937 cell line was used as a source of mRNA. This was prepared using standard procedures including guanidinium isothiocyanate/CsCl extraction as described by Chirgwin, J. M., et al., *Biochemistry* (1979) 18:5294, followed by isolation of mRNA on oligo(dT)-cellulose chromatography (Aviv, H., et al., *Proc Natl Acad Sci USA* (1972) 69:1408. The cDNA library was prepared from 5 ug of the isolated mRNA by the method of Gubler, U., et al., *Gene* (1983) 25:263 and cDNA inserts of greater than 1 kb were ligated into lambda-gt10 arms, packaged and plated on C600 hflA *E. coli* to obtain $2 \times 10^6$ recombinants. The cDNA library was probed with a $^{32}$P-labeled 64 degenerate 17-mer antisense oligonucleotide probe based on residues 7–12 of the MCP protein as determined by amino acid sequencing of the purified protein of Example 1. The 17-mer encoded the sequence Phe-Glu-Ala-Met-Glu-Leu. The library was probed on plaque lifts on nitrocellulose filters wherein the filters the filters were hybridized overnight at 37° C. in 6× SSC (1× SSC–0.15M sodium chloride/0.015M sodium citrate)/5× Denhardt's solution (1× Denhardt's= 0.02% BSA/0.02% Ficoll/0.02% polyvinylpyrrolidone)/ 0.05M sodium phosphate, pH 6.8, containing 100 ug sonicated herring sperm DNA and $5 \times 10^5$ cpm labeled probe per mil. The filters were washed two times for 30 min with 2× SSC/0.1% SDS at room temperature.

The plaques yielding positive signals in duplicate were plaque purified using standard methods.

The positive plaques were cloned into pUC-19 and sequenced using the standard dideoxy sequencing method. One clone which contained a 1.5 kb insert was sequenced with the results shown in FIG. 1.

As shown in FIG. 1, the cDNA contains an open reading frame encoding 384 amino acids. The first 34 amino acids are a typical structure for a signal peptide; the succeeding 24 amino acids match the N-terminal protein sequence determined by Edman degradation of the protein in Example 1. The putative protein without signal of 39 kd agrees with the size of the MCP precursor detected in biosynthetic studies by Ballard, L. L., et al., *Fed Proc* (1987) 46:773. It will be seen that there are 3 N-linked glycosylation sites and multiple potential O-linked glycosylation sites in the ser/thr-rich region (12/25 residues) between amino acids 253–277, consistent with the oligosaccharide structure of MCP as determined by Ballard et al., supra. Hydrophobicity analysis according to Hopp, T. P., et al., *Proc Natl Acad Sci USA* (1981) 78:3824 show a 23-amino acid region typical for a transmembrane hydrophobic domain at amino acids 295–317, followed by a 33-amino acid region corresponding to a cytoplasmic tail. The untranslated downstream region is consistent with a polyadenylation site.

However, the bulk of the protein at the N-terminus consists of 4 contiguous domains of about 60 amino acids which match the consensus sequence found in the multigene family of complement regulatory proteins. These 4 domains show 18–35% amino acid sequence homology to each other (29–44% if conservative amino acid sequences are allowed) similar to the degree of homology in other members of the family.

I claim:

1. A method to treat a disease or condition characterized by enhanced complement activity, which method comprises administering to a subject in need of such treatment an effective amount of isolated human membrane cofactor protein encoded by a DNA which hybridizes under stringent conditions to the complement of the DNA encoding amino acids 1–251 of FIG. 1 expressed in a non-human or human recombinant host cell in admixture with a suitable pharmaceutical excipient.

2. The method of claim 1 wherein the membrane cofactor protein has the amino acid sequence shown in FIG. 1 from amino acid residues 1 to 350 or an alternatively spliced version of this amino acid sequence.

3. The method of claim 1 wherein the host is selected from the group consisting of procaryotic cells, yeast cells, avian cells, and insect cells.

4. The method of claim 1 wherein the membrane cofactor protein is isolated from the surface of a non-human or human recombinant host cell that does not normally express membrane cofactor protein.

5. The method of claim 1 wherein the membrane cofactor protein contains one or two conservative substitutions of the amino acid sequence shown as amino acids 1–251 of FIG. 1.

6. The method of claim 1 wherein the disease or condition is characterized by inflammation.

* * * * *